United States Patent
Shin

(10) Patent No.: US 11,813,176 B2
(45) Date of Patent: Nov. 14, 2023

(54) SPINAL FUSION DEVICE

(71) Applicant: GS Solutions, Inc., Mission Viejo, CA (US)

(72) Inventor: Hanjin Shin, Mission Viejo, CA (US)

(73) Assignee: GS Solutions, Inc., Mission Viejo, CA (US)

( * ) Notice: Subject to any disclaimer, the term of this patent is extended or adjusted under 35 U.S.C. 154(b) by 0 days.

(21) Appl. No.: 17/518,095

(22) Filed: Nov. 3, 2021

(65) Prior Publication Data
US 2023/0157840 A1 May 25, 2023

Related U.S. Application Data

(60) Provisional application No. 63/109,663, filed on Nov. 4, 2020.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4601* (2013.01); *A61F 2/4611* (2013.01); *A61F 2/4637* (2013.01); *A61F 2002/30507* (2013.01)

(58) Field of Classification Search
None
See application file for complete search history.

(56) References Cited

U.S. PATENT DOCUMENTS

| | | | |
|---|---|---|---|
| 8,845,731 B2 | 9/2014 | Weiman | |
| 9,801,733 B2 | 10/2017 | Wolters et al. | |
| 10,137,009 B2 | 11/2018 | Weiman et al. | |
| 10,278,830 B1* | 5/2019 | Walker | A61F 2/4455 |
| 2014/0142701 A1* | 5/2014 | Weiman | A61F 2/4455 623/17.15 |
| 2015/0066031 A1* | 3/2015 | Ciupik | A61B 17/8822 606/93 |
| 2017/0181863 A1* | 6/2017 | Bjork | A61F 2/4611 |
| 2019/0321198 A1* | 10/2019 | Glerum | A61F 2/4611 |
| 2020/0085586 A1* | 3/2020 | Ludwig | A61F 2/4611 |

* cited by examiner

*Primary Examiner* — Tessa M Matthews

(57) ABSTRACT

A fusion device includes an actuator including a shaft, a receiver disposed posterior to the actuator and configured to be coupled to the shaft of the actuator, and a first plate and a second plate each slidably coupled to the actuator. The first and second plates are configured to move away from each other when the fusion device transitions from a first state to a second state.

16 Claims, 8 Drawing Sheets

SPINAL FUSION DEVICE

CROSS-REFERENCE TO RELATED APPLICATION

The present disclosure claims priority to U.S. provisional Application No. 63/109,663 filed on Nov. 4, 2020, which is incorporated by reference herein for all purposes.

BACKGROUND

Spine disorders often result in degeneration of the spinal disc in an intervertebral space between upper and lower vertebral bodies. Such a degenerated spinal disc may be treated by installing a fusion device into the intervertebral space and providing bone graft material through the installed fusion device to fuse the upper and lower vertebral bodies. While installing the fusion device, the fusion device may be susceptible to external forces applied thereto, which may result in structural failure of the fusion device. Facilitation of providing the bone graft material may be desirable to improve bone growth in fusing the upper and lower vertebral bodies.

SUMMARY

Embodiments of the present application relate to a fusion device and a process of using the fusion device to treat spinal disorders.

In an embodiment, a fusion device includes an actuator including a shaft, a receiver disposed posterior to the actuator and configured to be coupled to the shaft of the actuator, and a first plate and a second plate each slidably coupled to the actuator. The first and second plates are configured to move away from each other when the fusion device transitions from a first state to a second state.

In an embodiment, an implant includes an actuator including a hollow shaft, a receiver disposed posterior to the actuator and configured to be coupled to the hollow shaft of the actuator, a connector rotatably coupled to the receiver, and a first plate and a second plate each slidably coupled to the actuator and the connector. The first and second plates are configured to move away from each other when the fusion device transitions from a first state to a second state. The shaft has a through hole for delivering material therethrough, and the first state is a non-expanded state and the second state is an expanded state.

In an embodiment, a method of using a fusion device includes inserting a fusion device in a first state into a treatment region, transitioning the fusion device from the first state to a second state by inserting the hollow shaft of the actuator into the receiver, and injecting material through the channel of the fusion device to make the injected material flow out from the opening of the actuator.

DETAILED DESCRIPTION

Figure 1:
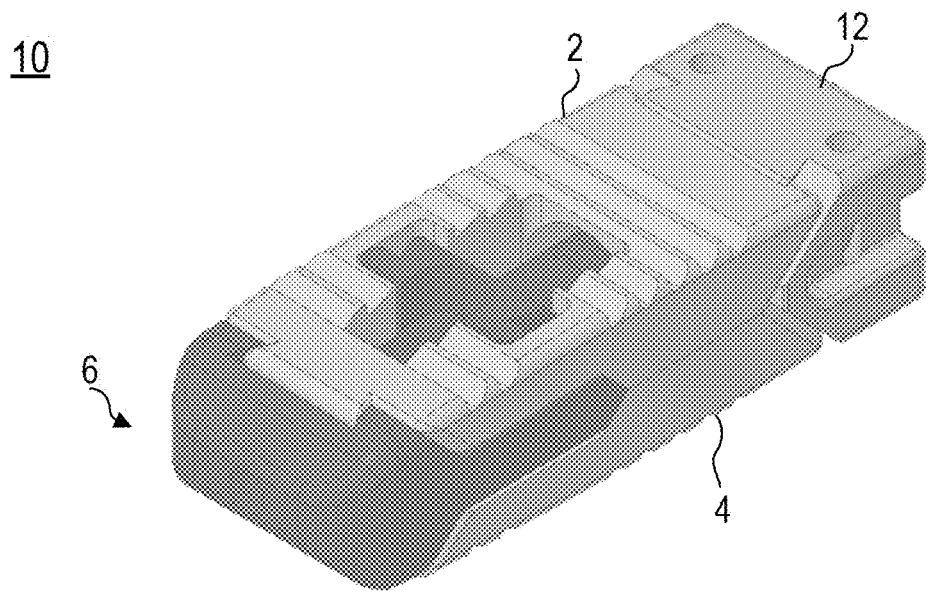
FIG. 1 and FIG. 2 illustrate a fusion device in a first state (e.g., a non-expanded state) and a second state (e.g., an expanded state), respectively, according to an embodiment of the present disclosure

Embodiments of the present application relate to a fusion device and a process of using the fusion device to treat spinal disorders.

In an embodiment, a fusion device (may also be referred to as, "implant" or "spinal device") includes an actuator including a shaft, a receiver disposed posterior to the actuator and configured to be coupled to the shaft of the actuator, a connector rotatably coupled to the receiver, and a first plate and a second plate each slidably coupled to the actuator and the connector. The first and second plates may move away from each other when the fusion device transitions from a first state (e.g., a non-expanded state) to a second state (e.g., an expanded state). Since the receiver is disposed posterior to the actuator and have a threaded inner surface to which an outer threaded surface of the hollow shaft is coupled, the receiver may have a relatively long longitudinal length to ensure structural reliability of the fusing device. The shaft may be hollow depending on implementation.

In an embodiment, the actuator further includes an anterior portion slidably coupled to the first plate and the second plate, a posterior portion, and an opening disposed between the anterior portion and the posterior portion. The opening may be sufficiently great to facilitate injection of material for improving bone growth (or bone fusion) in a fusion process, and sufficiently small to ensure the structural reliability of the fusing device.

In an embodiment, the receiver is configured to receive a set fastener to substantially fix a position of a posterior end of the hollow shaft of the actuator, thereby locking the fusion device at a desired height. Since the set fastener and the receiver together may provide a robust locking mechanism for the hollow shaft, the position of the posterior end of the hollow shaft may be substantially fixed to maintain an expanded height of the actuator at a target value while ensuring the structural reliability of the fusion device.

In an embodiment, a method of using a fusion device includes inserting the fusion device in a non-expanded state into a treatment region, transitioning the fusion device from the non-expanded state to an expanded state by inserting a hollow shaft of the actuator into the receiver, and injecting material through a channel of the fusion device to make the injected material flow out from an opening of the actuator. In an embodiment, the injected material may be bone graft material, bone morphogenic protein, or other materials, or a combination thereof, that may be used to facilitate the fusing of the fusion device to the bone (hereinafter, referred to as "fusing material.")

A detailed description of embodiments is provided below along with accompanying figures. The scope of this disclosure is limited only by the claims and encompasses numerous alternatives, modifications and equivalents. Although steps of various processes are presented in a given order, embodiments are not necessarily limited to being performed in the listed order. In some embodiments, certain operations may be performed simultaneously, in an order other than the described order, or not performed at all.

Numerous specific details are set forth in the following description. These details are provided to promote a thorough understanding of the scope of this disclosure by way of specific examples, and embodiments may be practiced according to the claims without some of these specific details. Accordingly, the specific embodiments of this disclosure are illustrative, and are not intended to be exclusive or limiting. For the purpose of clarity, technical material that is known in the technical fields related to this disclosure has not been described in detail so that the disclosure is not unnecessarily obscured.

Figure 2:
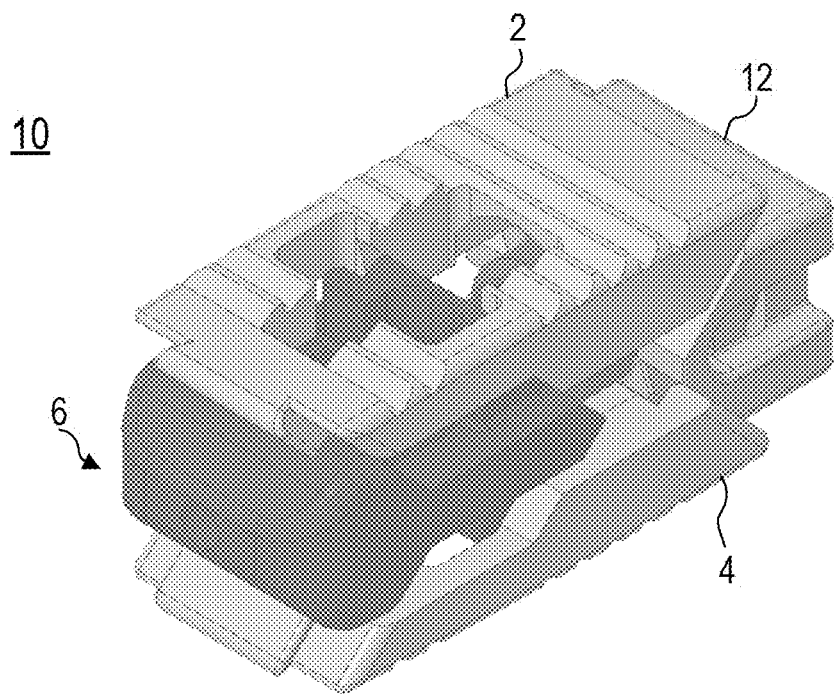
Figure 3A:
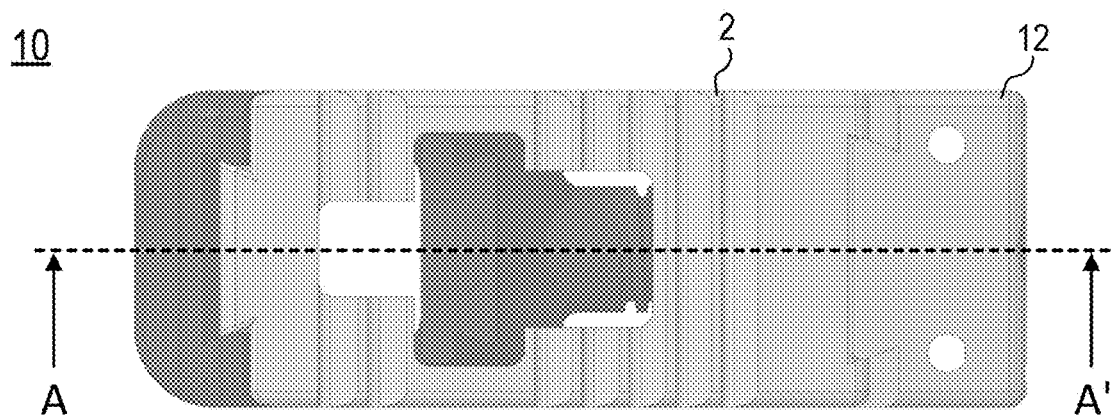
FIGS. 3A, 3B, and 3C illustrate a top view, a cross-sectional view, and a rear view of the fusion device of FIG. 1 in the non-expanded state, according to an embodiment of the present disclosure.
Figure 3B:
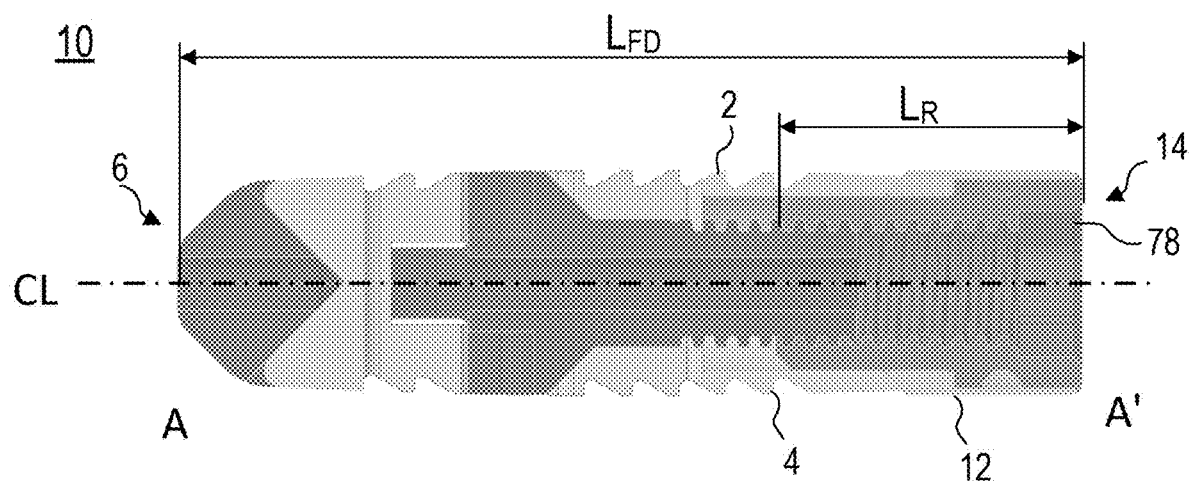
Figure 3C:
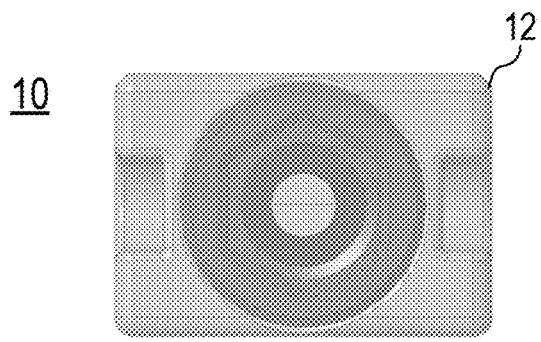
Figure 4A:
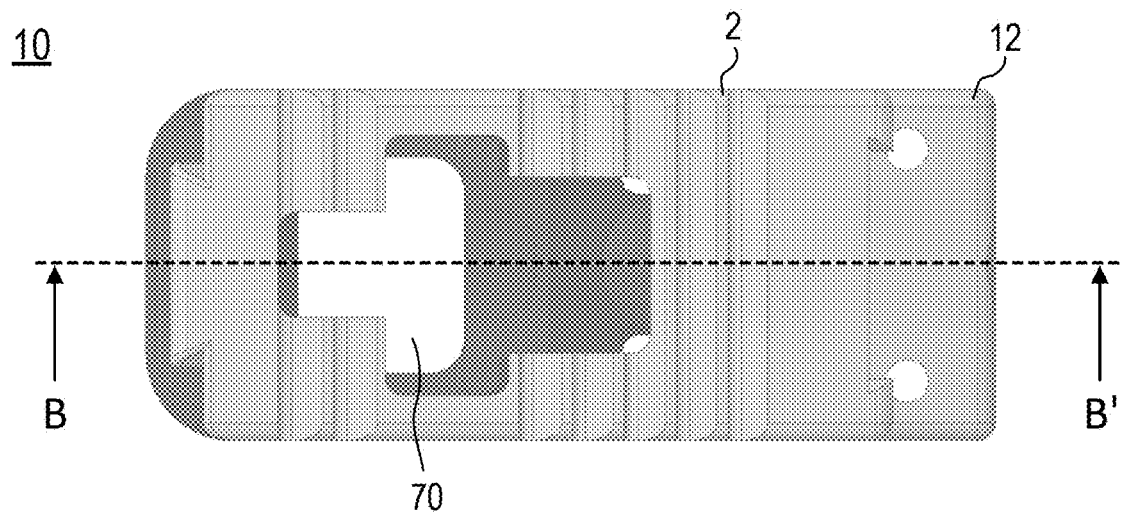
FIGS. 4A, 4B, and 4C illustrate a top view, a cross-sectional view, and a rear view of the fusion device of FIG. 2 in the expanded state, according to an embodiment of the present disclosure.
Figure 4B:
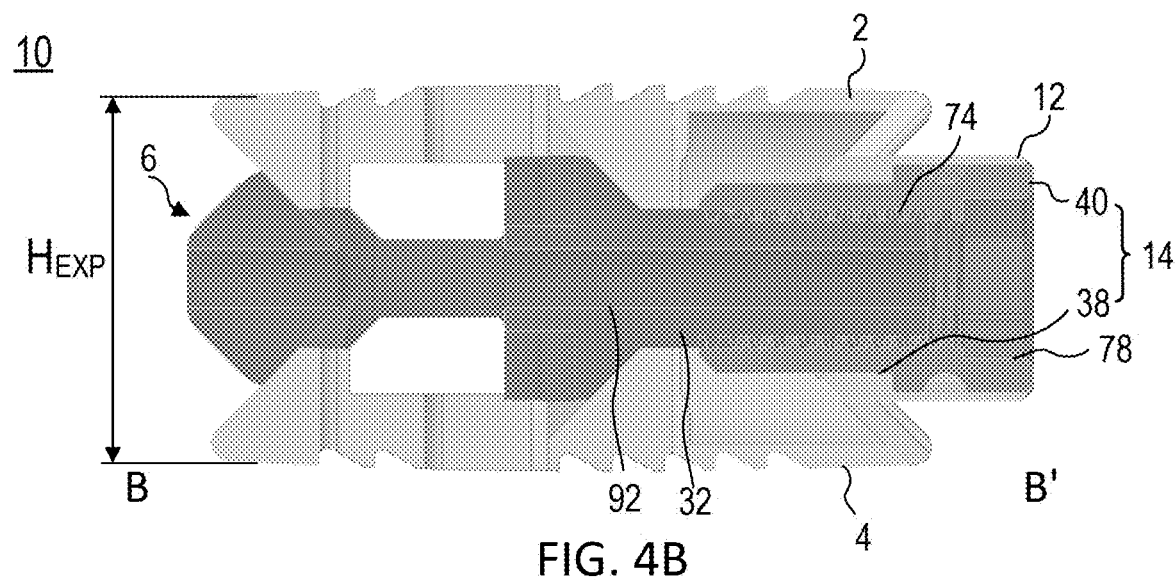
Figure 4C:
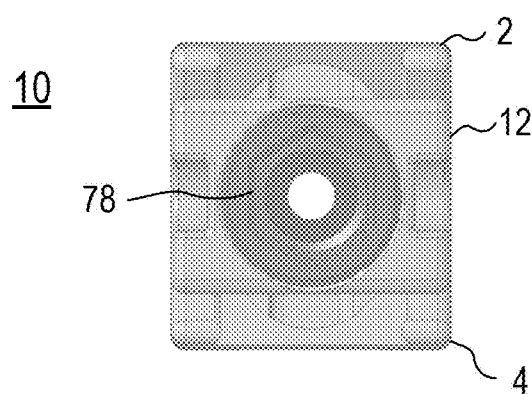
Figure 5:
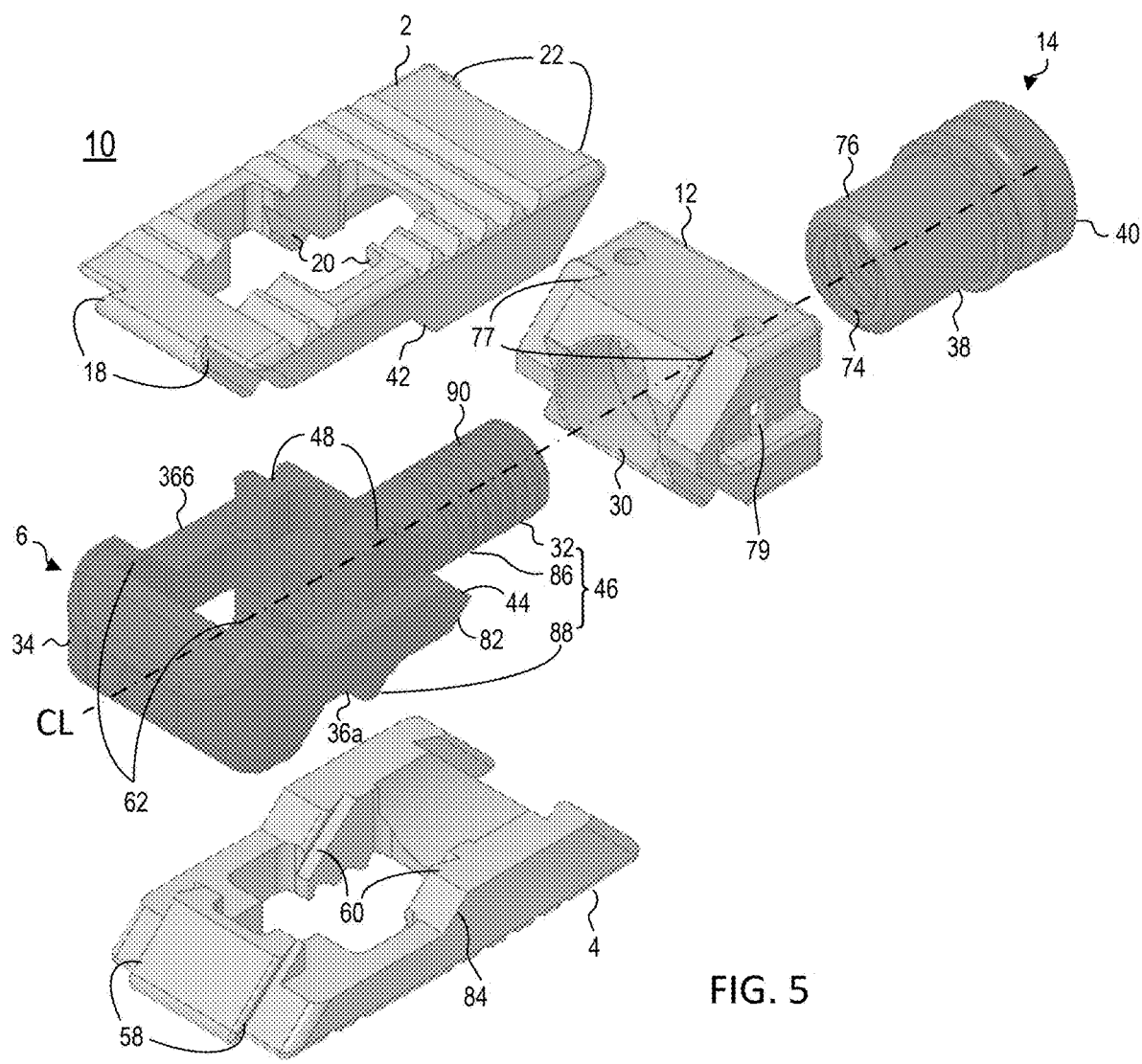
FIG. 5 illustrates an exploded view of the fusion device of FIGS. 1 and 2 according to an embodiment of the present disclosure.
Figure 6:
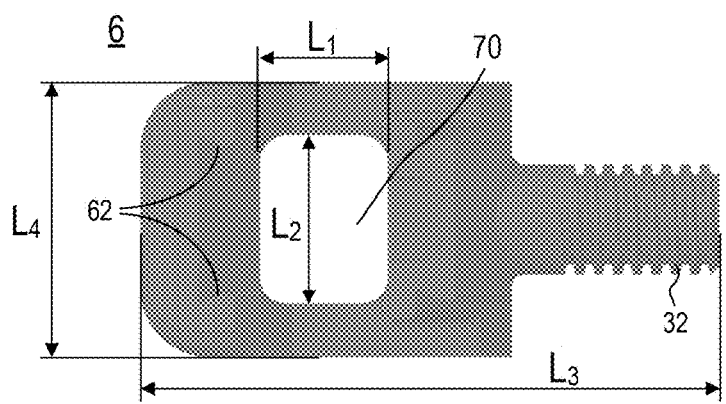
FIG. 6 illustrates a top view of an actuator of the fusion device of FIGS. 1 and 2 according to an embodiment of the present disclosure.

FIG. 1 and FIG. 2 illustrate a fusion device 10 in a first state (e.g., a non-expanded state) and a second state (e.g., an expanded state), respectively, according to an embodiment of the present disclosure. FIGS. 3A, 3B, and 3C illustrate a top view, a cross-sectional view, and a rear view of the fusion device 10 in the non-expanded state, respectively, according to an embodiment of the present disclosure. For example, the cross-sectional view shown in FIG. 3B of the fusion device 10 may be obtained by cutting the fusion device 10 along a line A-A' shown in FIG. 3A. FIGS. 4A, 4B, and 4C illustrate a top view, a cross-sectional view, and a rear view of the fusion device 10 in the expanded state, respectively, according to an embodiment of the present disclosure. For example, the cross-sectional view shown in FIG. 4B of the fusion device 10 may be obtained by cutting the fusion device 10 along a line B-B' shown in FIG. 4A. FIG. 5 illustrates an exploded view of the fusion device 10 according to an embodiment of the present disclosure. FIG. 6 illustrates a top view of an actuator 6 included in the fusion device 10 according to an embodiment of the present disclosure.

Figure 7:
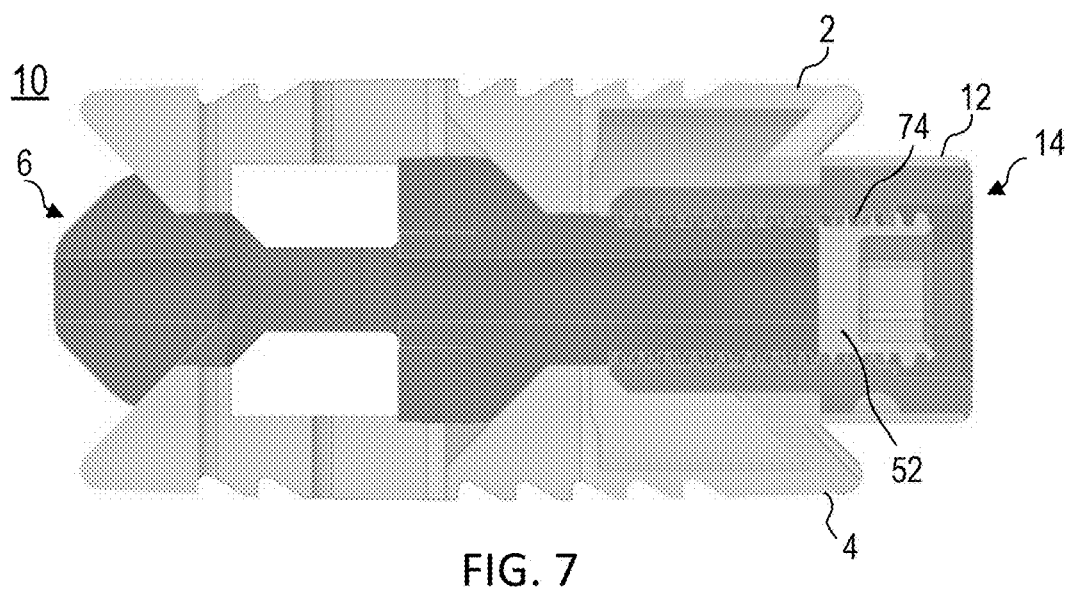
FIG. 7 illustrates a fusion device locked in an expanded state using a set fastener according to an embodiment of the present disclosure.
Figure 8A:
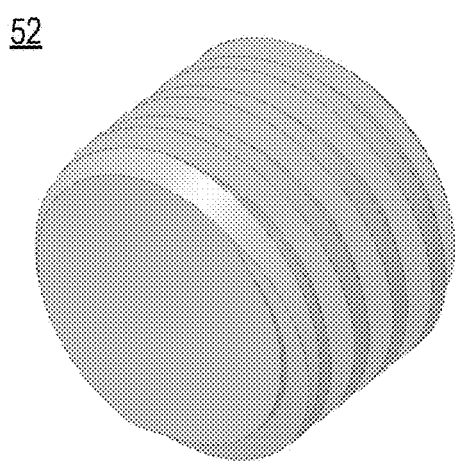
FIGS. 8A, 8B, and 8C illustrate a perspective view, a side view, and a rear view of the set fastener of FIG. 7 according to an embodiment of the present disclosure.
Figure 8B:
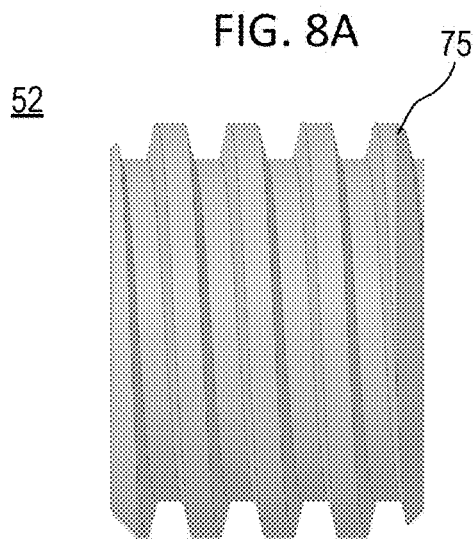
Figure 8C:
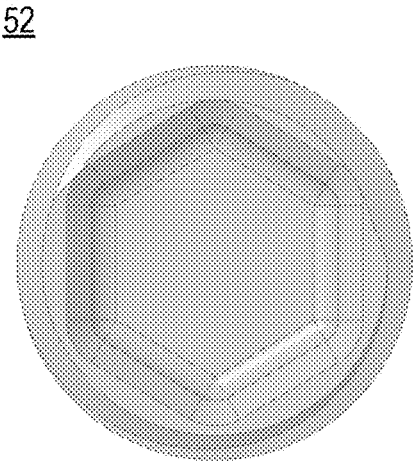

Referring to FIGS. 5 and 6, the fusion device 10 includes a first plate 2 (e.g., an upper plate), a second plate (e.g., a lower plate) 4, an actuator 6, a connector 12, and a receiver 14. A set fastener (or set screw) 52 (see FIG. 7) may be inserted into the receiver 14 to lock the fusion device 10 at a given expanded state.

The actuator 6 may include an anterior portion 34, first and second side portions 36a and 36b, and a posterior portion 46. In an embodiment, the anterior portion 34 of the actuator 6 may include a pair of upper grooves 62 slidably coupled to a pair of first grooves 18 of the first plate 2, and a pair of lower grooves (not shown) slidably coupled to a pair of first grooves 58 of the second plate 4. The anterior portion 34 may further include a through hole 48 through which a guide wire may be inserted. As explained below, the through hole may also be used to inject fusing material therethrough.

The first and side portions 36a and 36b of the actuator 6 may couple the anterior portion 34 and the posterior portion 46, such that a posterior end of the anterior portion 34, inner side surfaces of the first and second side portions 36a and 36b, and an anterior end of the posterior portion 46 define an opening 70. Each of the first and second side portions 36a and 36b may have an upper ramp surface 44 and a lower ramp surface 82 that are slidably coupled to a ramp surface 42 of the first plate 2 and a ramp surface 84 of the second plate 4, respectively.

The posterior portion 46 of the actuator 6 may include a first wedge (e.g., an upper wedge) 86 and a second wedge (e.g., a lower wedge) 88 that are slidably coupled to the first and second plates 2 and 4, respectively. For example, the upper wedge 86 of the posterior portion 46 may include a pair of upper grooves 48 that are slidably coupled to a pair of grooves 20 of the first plate 2.

The posterior portion 46 may further include a hollow shaft 32 that extends in a longitudinal direction along a centerline CL of the fusion device 10. In an embodiment, the hollow shaft 32 has a threaded outer surface 90 to be coupled to an inner surface 74 of the receiver 14. For example, the outer surface 90 of the hollow shaft 32 may have a male thread and the inner surface 74 of the receiver 14 may have a female thread. However, embodiments of the present disclosure are not limited thereto.

The receiver 14 may include a first portion 38. The first portion 38 of the receiver 14 may have the inner surface 74 coupled to the outer surface 90 of the hollow shaft 32 and an outer surface 76 rotatably coupled to a through hole 30 of the connector 12. Since the receiver 14 may be disposed posterior to the actuator 6 and have the threaded inner surface 74 to which the outer threaded surface 90 of the hollow shaft 32 is coupled, the receiver 14 may have a relatively long length in the longitudinal direction. For example, referring to FIG. 3B illustrating the fusion device 10 in the non-expanded state, a longitudinal length $L_R$ of the receiver 14 along the centerline CL may be in a range from 25% to 45% of a longitudinal length $L_{FD}$ of the fusion device 10 along the centerline CL. When the longitudinal length $L_R$ of the receiver 48 is shorter than 25% of the longitudinal length $L_{FD}$ of the fusion device 10, the hollow shaft 32 of the actuator 6 may not be inserted into the receiver 14 with a sufficient depth to ensure the structural reliability of the fusion device 10. When the longitudinal length $L_R$ of the receiver 48 exceeds 45% of the longitudinal length $L_{FD}$ of the fusion device 10, a size of the opening 70 of the actuator 6 may be reduced to such a degree that the size is not sufficiently large to facilitate injection of fusing material, as will be described below in more detail. In an embodiment, the longitudinal length $L_R$ of the receiver 14 along the centerline CL is at least 30% of the longitudinal length $L_{FD}$ of the fusion device 10 along the centerline CL. In another embodiment, the longitudinal length $L_R$ of the receiver 14 along the centerline CL is at least 35% of the longitudinal length $L_{FD}$ of the fusion device 10 along the centerline CL. In yet another embodiment, the longitudinal length $L_R$ of the receiver 14 along the centerline CL is at least 40% of the longitudinal length $L_{FD}$ of the fusion device 10 along the centerline CL.

The receiver 14 may further include a second portion 40 disposed posterior to the first portion 38. The second portion 40 of the receiver 14 may have an inner surface 78 with a cross-sectional shape matching that of an end of a driving tool for rotating the receiver 14. In an embodiment, the second portion 40 may have a polygon shape with a size (e.g., a distance between opposite sides of the polygon shape) greater than a size (e.g., a major diameter of the internal thread) of the inner surface 74 of the first portion 38.

After the fusion device 10 has been placed in a treatment region (e.g., a damaged intervertebral disc space), the insertion driver may be inserted into the second portion 40 of the receiver 14 to rotate the receiver 14 in a given rotational direction, thereby causing the actuator 6 to move along the centerline CL in a posterior direction to increase a length of a portion of the hollow shaft 32 inserted into the first portion 38 of the receiver 14. As a result, the actuator 6 drives the first and second plates 2 and 4 away from the centerline CL of the fusion device 10, leading to the expanded state of the fusion device 10 shown in FIGS. 2 and 4A-4C. For example, the length of the inserted portion of the hollow shaft 32 may be adjusted until an expanded height (e.g., a height $H_{EXP}$ between a bottom surface of the second plate 4 and an upper surface of the first plate 2 in FIG. 4B) of the actuator 6 reaches a desired height.

Once expanded to reach the desired height, fusing material may be provided to the fusion device 10. For example, an injecting device (not shown) may be inserted into the receiver 14 to inject the fusing material through the through hole 92 of the hollow shaft 32, and the injected fusing material may flow out from the opening 70 of the actuator 6. In an embodiment, the opening 70 of the actuator 6 may be sufficiently great to facilitate the injection of the fusing material, thereby improving the bone growth in the fusion process. In addition, the opening 70 of the actuator 6 may be sufficiently small to ensure the structural reliability of the actuator 60. For example, referring to FIG. 6 illustrating a top view of the actuator 6, when the opening 70 may have a first length $L_1$ in a longitudinal direction of the actuator 6 and a second length $L_2$ in a direction perpendicular to the longitudinal direction, the first length $L_1$ of the opening 70 may be in a range from 15% to 30% of a total length $L_3$ of the actuator 6 in the longitudinal direction, and the second length $L_2$ of the opening 70 may be in a range from 50% to 70% of a total length $L_4$ of the actuator 6 in the direction perpendicular to the longitudinal direction. In an embodiment, the first length $L_1$ of the opening 70 is at least 20% (e.g., about 22%) of a total length $L_3$ of the actuator 6 in the longitudinal direction, and the second length $L_2$ of the opening 70 is at least 58% (e.g., about 60%) of a total length $L_4$ of the actuator 6 in the direction perpendicular to the longitudinal direction. In another embodiment, the first length $L_1$ of the opening 70 is at least 25% of a total length $L_3$ of the actuator 6 in the longitudinal direction, and the second length $L_2$ of the opening 70 is at least 63% of a total length $L_4$ of the actuator 6 in the direction perpendicular to the longitudinal direction.

Once the injection of the fusing material has been complete, a set fastener (e.g., the set fastener 52 in FIG. 7) may be inserted into the receiver 14. For example, referring to FIG. 7, the set fastener 52 may be inserted until an anterior end of the set fastener 52 contacts a posterior end of the hollow shaft 32. Since the set fastener 52 and the receiver 14 together may provide a robust locking mechanism for the hollow shaft 32, the position of the posterior end of the hollow shaft 32 may be substantially fixed to maintain the expanded height of the actuator 6 at the desired height while ensuring the structural reliability of the fusion device 10. In an embodiment, the set fastener 52 may have a threaded outer surface to be inserted into the receiver 14. For example, referring to FIGS. 7 and 8A to 8C, the set fastener 52 may have a threaded outer surface 75 to be coupled to the inner surface 74 of the receiver 14.

Figure 9:
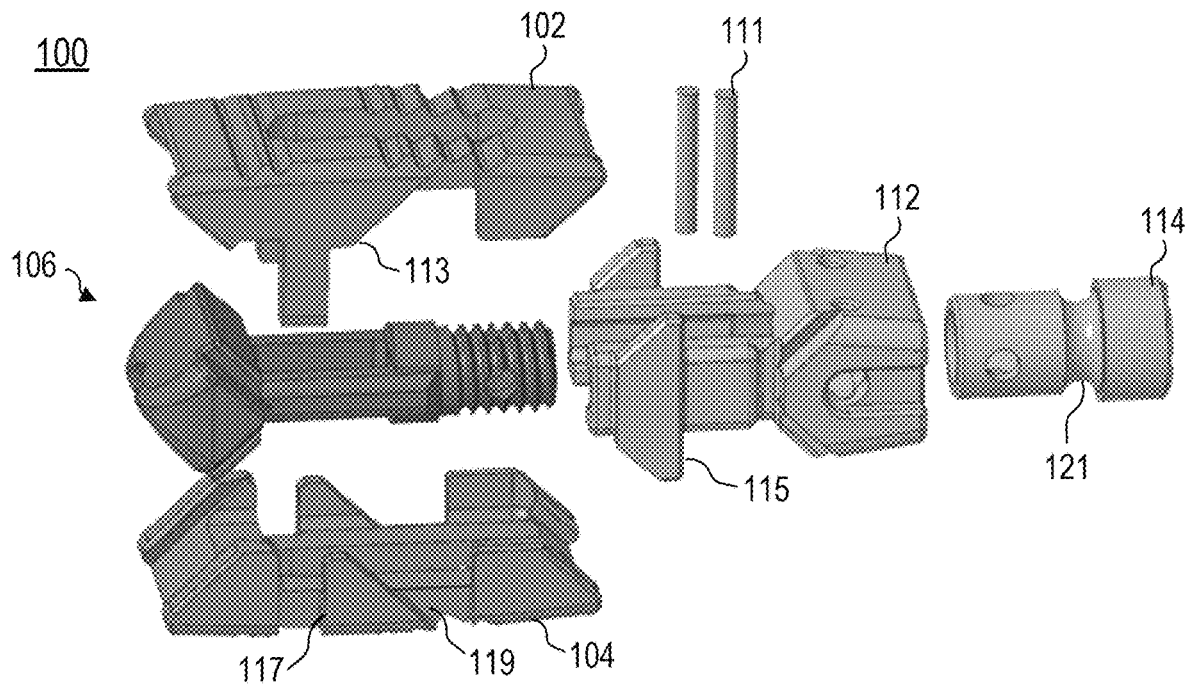
FIG. 9 illustrates an exploded view of a fusion device according to an embodiment of the present disclosure.

FIG. 9 illustrates an exploded view of a fusion device 100 according to an embodiment of the present disclosure. The fusion device 100 includes a first plate 102, a second plate 104, an actuator 106, a connector 112, and a receiver 114, and one or more pins 111. Descriptions on structural and functional features of the fusion device 100 similar to those of the fusion device 10 in FIGS. 1 to 6 may be omitted for the interest of brevity.

The fusion device 100 in FIG. 9 differs from the fusion device 10 in FIGS. 1 to 6 in that the first plate 102 and the second plate 104 of the fusion device 100 have different structures from each other, whereas the first plate 2 and second plate 4 of the fusion device 10 have substantially the same structure. For example, the first plate 102 of the fusion device 100 has a side portion 113 slidably coupled to a first recess 117 of the second plate 104. The fusion device 100 in FIG. 9 also differs from the fusion device 10 in FIGS. 1 to 6 in that the connector 112 of the fusion device 100 includes a side portion 115 slidably coupled to the side portion 113 of the first plate 102 and a second recess 119 of the second plate 104. In addition, the fusion device 100 in FIG. 9 differs from the fusion device 10 in FIGS. 1 to 6 in that the pins 111 are received by the connector 112 to engage a neck 121 of the receiver 114, thereby retaining the receiver 114 within the connector 112 while allowing the receiver 114 to rotate for expanding the fusion device 100.

Figure 10:
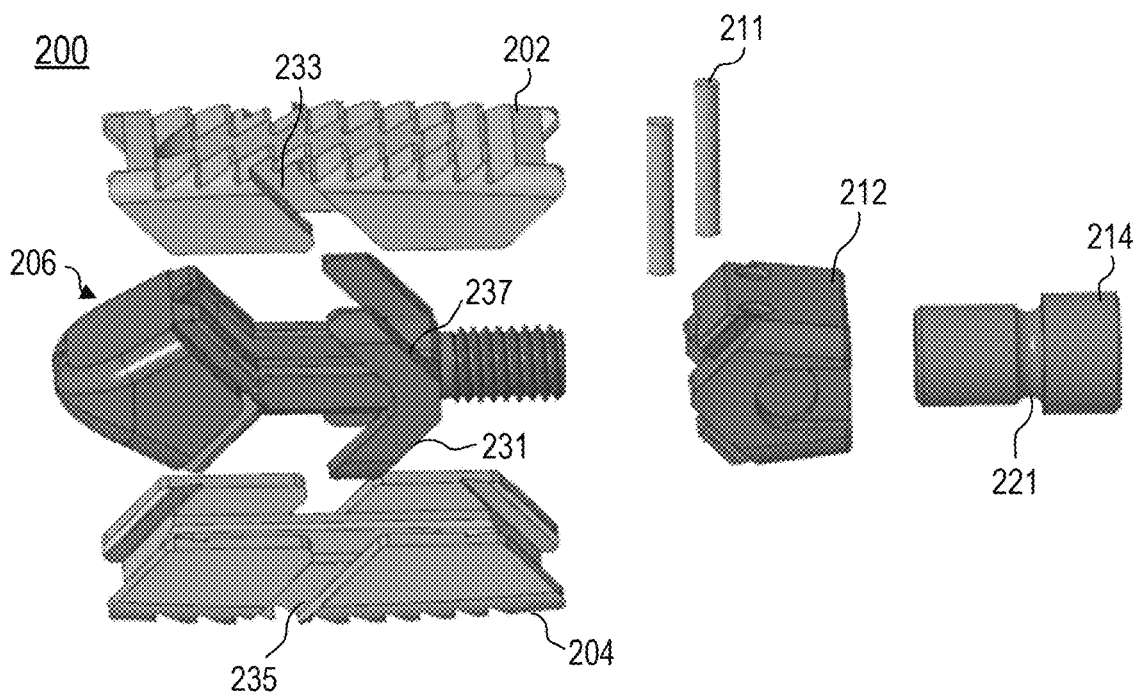
FIG. 10 illustrates an exploded view of a fusion device according to an embodiment of the present disclosure.

FIG. 10 illustrates an exploded view of a fusion device 200 according to an embodiment of the present disclosure. The fusion device 200 includes a first plate 202, a second plate 204, an actuator 206, a connector 212, and a receiver 214, and one or more pins 211. Descriptions on structural and functional features of the fusion device 200 similar to those of the fusion device 10 in FIGS. 1 to 6 may be omitted for the interest of brevity.

The fusion device 200 in FIG. 10 differs from the fusion device 10 in FIGS. 1 to 6 in that the actuator 206 of the fusion device 200 includes a side upper portion 237 and a side lower portion 231 each extending in an oblique direction with respect to a longitudinal direction of the actuator 206, and that the first plate 202 and the second plate 204 include recesses 233 and 235 slidably coupled to the side upper and lower portions 237 and 231, respectively. In addition, the fusion device 200 in FIG. 10 differs from the fusion device 10 in FIGS. 1 to 6 in that the pins 211 functions to engage a neck 221 of the receiver 214, thereby retaining the receiver 214 within the connector 212 while allowing the receiver 214 to rotate for expanding the fusion device 200.

Figure 11:
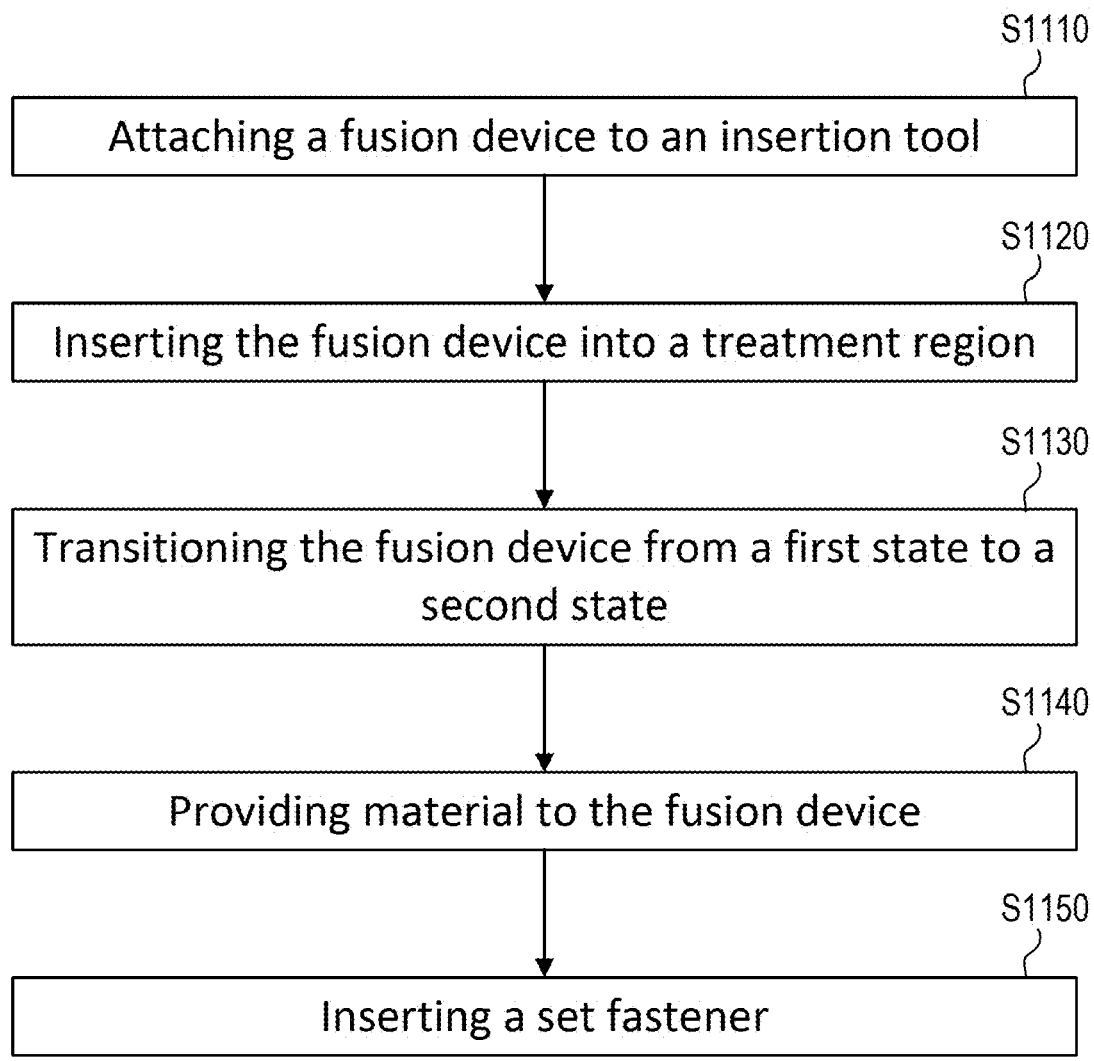
FIG. 11 is a flowchart illustrating a process of using a fusion device to treat spinal disorders according to an embodiment.

FIG. 11 is a flowchart illustrating a process of using a fusion device (e.g., the fusion device 10 in FIGS. 1 to 6) to treat spinal disorders according to an embodiment. In an embodiment, such treatment may be a Posterior Lumbar Interbody Fusion (PLIF) surgery.

Figure 12:
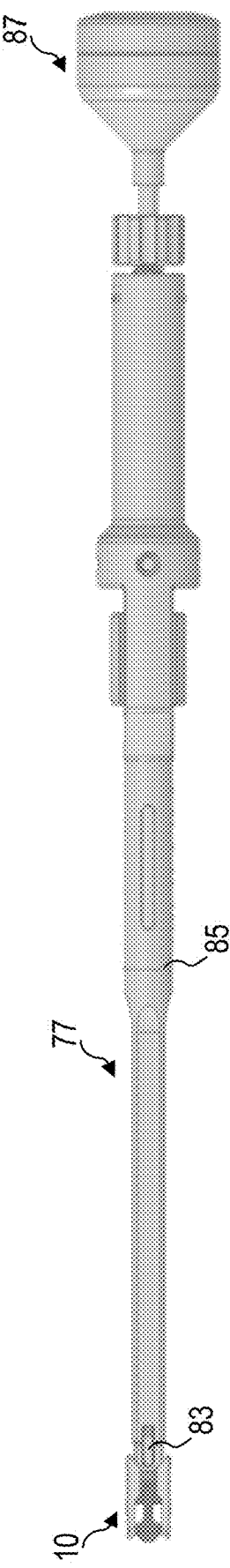
FIG. 12 illustrates an insertion tool used to insert a fusion device according to an embodiment of the present disclosure.

At S1110, the fusion device in a first state (e.g., the non-expanded state) may be attached to an insertion tool. In an embodiment, such an insertion tool may include a pair of prongs to be inserted into corresponding holes (e.g., side holes 79 of the connector 12 in FIG. 5) of the fusion device for attaching the fusion device to the insertion tool. FIG. 12 illustrates an insertion tool 77 according to an embodiment of the present disclosure. For example, the insertion tool 77 may include a sleeve 85 and an inserter body having a pair of prongs 83 and passing through the sleeve 85. The insertion tool 77 may be coupled to an injecting device 87 used to inject fusing material as will be described below in more detail.

At S1120, the fusion device in the first state may be inserted into a treatment region (e.g., a damaged intervertebral disc space) using the insertion tool. In an embodiment, a portion of the insertion tool may be removed and the remaining portion of the insertion tool may be coupled with a structure suitable for applying an external force thereon. For example, the structure may have a posterior end having a relatively large cross-sectional area onto which a hammer strikes to exert the external force.

At S1130, the fusion device may transition from the first state to a second state (e.g., the expanded state). In an embodiment, a portion (e.g., the hollow shaft 32 in FIGS. 4B and 5) of an actuator (e.g., the actuator 6 in FIGS. 4B and 5) may be inserted into the receiver by a given distance to adjust a height (e.g., the expanded height $H_{EXP}$ in FIG. 4B) of the fusion device to a desired height (or target value). For example, a driving tool may be inserted into a receiver (e.g., the receiver 14 in FIGS. 1 to 6) to rotate the receiver in a given rotational direction, thereby driving first and second plates (e.g., the upper and lower plates 2 and 4 in FIGS. 1 to 6) away from each other until the adjusted height of the fusion device reaches the target value.

At S1140, material may be provided to the fusion device. In an embodiment, an injecting device (e.g., the injecting device 87 in FIG. 12) may be inserted into the receiver to inject fusing material into a channel (e.g., the through hole 92 of the hollow shaft 32 in FIG. 4B). Such a channel may be used to deliver the fusing material therethrough and be exposed to an opening (e.g., the opening 70 of the actuator 6 in FIG. 6), and thus the injected material through the channel may flow out from the opening.

At S1150, a set fastener (e.g., the set fastener 52 in FIG. 7) may be inserted into the receiver. In an embodiment, the set fastener may have a threaded outer surface (e.g., the threaded outer surface 75 in FIGS. 8B) to be coupled to a threaded inner surface (e.g., the inner surface 74 in FIG. 7) of the receiver, leading to a robust locking mechanism for a portion (e.g., the hollow shaft 32 of the actuator 6 inserted into the receiver 14 in FIG. 4B) of the actuator inserted into the receiver. In an embodiment, the fusion device may be locked in a desired height without the set fastener, in which case step S1150 may be performed optionally.

Aspects of the present disclosure have been described in conjunction with the specific embodiments thereof that are proposed as examples. Numerous alternatives, modifications, and variations to the embodiments as set forth herein may be made without departing from the scope of the claims set forth below. Accordingly, embodiments as set forth herein are intended to be illustrative and not limiting.

What is claimed is:

1. A fusion device, comprising:
   an actuator including a hollow shaft with an outer threaded surface;
   a receiver disposed posterior to the actuator and including a first portion and a second portion disposed posterior to the first portion, the first portion having a first inner surface that is an inner threaded surface and configured to be coupled to the shaft of the actuator, the second portion having a second inner surface connected to the first inner surface;
   a first plate and a second plate each slidably coupled to the actuator, the first and second plates being configured to move away from each other when the fusion device transitions from a first state to a second state;
   a connector rotatably coupled to the receiver,
   wherein each of the first and second plates is slidably coupled to the actuator and the connector.

2. The fusion device of claim 1, wherein the shaft has a through hole, the shaft being configured to be inserted into the first inner surface of the receiver.

3. The fusion device of claim 1, wherein the shaft has a through hole and the first state is a non-expanded state and the second state is an expanded state, and a longitudinal length of the receiver is in a range from 25% to 45% of a longitudinal length of the fusion device in the non-expanded state.

4. The fusion device of claim 1, wherein the second portion of the receiver has the second inner surface with a size greater than that of the inner threaded surface of the first portion.

5. The fusion device of claim 1, wherein the actuator further includes:
   an anterior portion slidably coupled to the first plate and the second plate;
   a posterior portion including the hollow shaft, a first wedge, and a second wedge, the first wedge and the second wedge being slidably coupled to the first plate and the second plate, respectively, the hollow shaft having a through hole;
   a pair of side portions coupling the anterior portion and the posterior portion; and
   an opening defined by the anterior portion, the posterior portion, and the pair of side portions, the opening being connected to the through hole of the hollow shaft.

6. The fusion device of claim 5, wherein a first length of the opening in a longitudinal direction of the actuator is in a range from 15% to 30% of that of the actuator in the longitudinal direction, and
   wherein a second length of the opening in a direction perpendicular to the longitudinal direction of the actuator is in a range from 50% to 70% of that of the actuator in the direction perpendicular to the longitudinal direction.

7. The fusion device of claim 5, wherein the receiver is configured to be coupled to an injecting device to inject fusing material, and the through hole of the shaft is to deliver the fusing material therethrough.

8. The fusion device of claim 1, wherein the receiver is configured to receive a set fastener to substantially fix a position of a posterior end of the hollow shaft, thereby locking the fusion device at a desired height.

9. The fusion device of claim 8, wherein the set fastener has a threaded outer surface configured to be coupled to the inner threaded surface of the first surface of the first portion of the receiver.

10. The fusion device of claim 8, wherein the connector is slidably coupled to the first plate and the second plate and includes a pair of side holes configured to receive a pair of prongs of an insertion tool.

11. The fusion device of claim 8, further comprising one or more pins configured to keep the receiver within the connector by engaging with a neck of the receiver,
   wherein the first plate includes a portion slidably coupled to a recess of the second plate, and
   wherein the actuator includes a first upper portion and a lower portion each extending in an oblique direction with respect to a centerline of the actuator, the upper portion and the lower portion being slidably coupled to the first plate and the second plate, respectively.

12. An implant, comprising:
   an actuator including a hollow shaft with an outer threaded surface;
   a receiver disposed posterior to the actuator and including a first portion and a second portion disposed posterior to the first portion, the first portion having a first inner surface that is an inner threaded surface and configured to be coupled to the hollow shaft of the actuator, the second portion having a second inner surface connected to the first inner surface;

a connector rotatably coupled to the receiver; and a first plate and a second plate each slidably coupled to the actuator and the connector, the first and second plates being configured to move away from each other when the fusion device transitions from a first state to a second state, wherein the shaft has a through hole for delivering material therethrough, and wherein the first state is a non-expanded state and the second state is an expanded state.

13. A method for using a fusion device, wherein the fusion device comprises an actuator and a receiver disposed posterior to the actuator, the actuator including a hollow shaft with an outer threaded surface, a channel, and an opening, the receiver including a first portion and a second portion disposed posterior to the first portion, the first portion having a first inner surface that is an inner threaded surface and configured to be coupled to the shaft of the actuator, the second portion having a second inner surface connected to the first inner surface, the method comprising:

inserting the fusion device in a first state into a treatment region;

transitioning the fusion device from the first state to a second state by inserting the hollow shaft of the actuator into the receiver;

injecting material through the channel of the fusion device to make the injected material flow out from the opening of the actuator; and inserting a set fastener into the receiver to substantially fix a position of a posterior end of the inserted hollow shaft.

14. The method of claim 13, wherein a longitudinal length of the receiver is in a range from 25% to 45% of a longitudinal length of the fusion device in the non-expanded state, and wherein the first state is a non-expanded state and the second state is an expanded state, wherein the material is fusing material.

15. The method of claim 13, wherein a first length of the opening in a longitudinal direction of the actuator is in a range from 15% to 30% of that of the actuator in the longitudinal direction, and wherein a second length of the opening in a direction perpendicular to the longitudinal direction of the actuator is in a range from 50% to 70% of that of the actuator in the direction perpendicular to the longitudinal direction.

16. The method of claim 13, further comprising:

attaching the fusion device in the non-expanded state to an insertion tool.

* * * * *